United States Patent

Curtis et al.

[11] Patent Number: 5,830,901
[45] Date of Patent: Nov. 3, 1998

[54] TETRAHYDROPYRIDINYLMETHYL DERIVATIVES OF PYRROLO[2,3-B] PYRIDINE

[75] Inventors: Neil Roy Curtis, Puckeridge; Janusz Jozef Kulagowski, Bishops Stortford; Paul David Leeson, Cambridge; Mark Peter Ridgill, Watton At Stone, all of United Kingdom

[73] Assignee: Merch Sharp & Dohme Ltd, Hoddesdon

[21] Appl. No.: 776,486

[22] PCT Filed: Aug. 1, 1995

[86] PCT No.: PCT/GB95/01820

§ 371 Date: Jan. 27, 1997

§ 102(e) Date: Jan. 27, 1997

[87] PCT Pub. No.: WO96/05200

PCT Pub. Date: Feb. 22, 1996

[30] Foreign Application Priority Data

Aug. 10, 1994 [GB] United Kingdom .................. 9416160
Aug. 10, 1994 [GB] United Kingdom .................. 9416161
Mar. 23, 1995 [GB] United Kingdom .................. 9505888

[51] Int. Cl.$^6$ ........................ A61K 31/44; C07D 471/02; C07D 491/02; C07D 498/02
[52] U.S. Cl. ............................................ 514/300; 546/113
[58] Field of Search ............................ 546/113; 514/300

[56] References Cited

U.S. PATENT DOCUMENTS 5,563,150 10/1996 Curtis et al. ............................ 514/300

FOREIGN PATENT DOCUMENTS 044254   10/1980  United Kingdom .
WO 94/20459  9/1994  WIPO .

OTHER PUBLICATIONS

Bottcher, H. et al. J. Med. Chem. "Synthesis and Dopaminergic Activity of Some 3-(1,2,3,6-Tetrahydro-1-pyridylalky)indoles. A Novel Conformational Model To Explani Structure-Activity Relationships" 1992, 35 pp. 4020-4026.
PCT International Search Report dated Oct. 13, 1995.

Primary Examiner—Mukund J. Shah
Assistant Examiner—Bruck Kifle
Attorney, Agent, or Firm—R. J. North; Melvin Winokur

[57] ABSTRACT

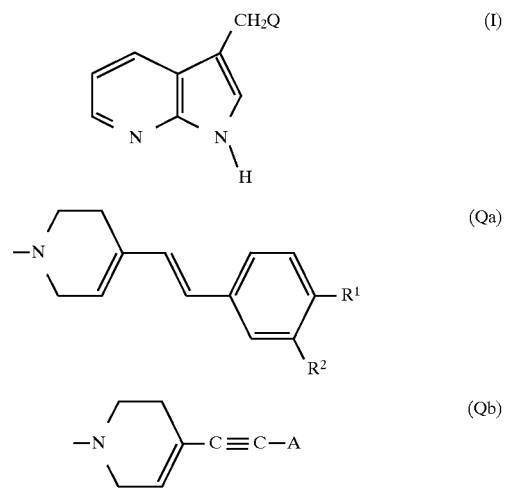

Disclosed is a class of pyrrolo[2,3-b]pyridine derivatives of formula (I) wherein Q represents a moiety of formula Qa or Qb, which are ligands for dopamine receptor subtypes within the body, in particular the dopamine D4 receptor subtype and are therefore useful in the treatment and/or prevention of disorders of the dopamine system, including schizophrenia.

13 Claims, No Drawings

TETRAHYDROPYRIDINYLMETHYL DERIVATIVES OF PYRROLO[2,3-B] PYRIDINE

This invention relates to a particular class of heteroaromatic compounds. More particularly, the invention is concerned with certain substituted tetrahydropyridinylmethyl derivatives of pyrrolo[2,3-b]-pyridine. These compounds are ligands for dopamine receptor subtypes within the body, in particular the dopamine $D_4$ receptor subtype. They are therefore of use in the treatment and/or prevention of disorders of the dopamine system, including schizophrenia, depression, anxiety, nausea, Parkinson's disease, tardive dyskinesias and extrapyramidal side-effects associated with treatment by conventional neuroleptic agents, neuroleptic malignant syndrome, disorders of hypothalamic-pituitary function such as hyperprolactinaemia and amenorrhoea, and delusional disorders (cf. Catalano et al., *Biol. Psychiatry*, 1993, 34, 459).

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

By virtue of their activity as ligands for dopamine receptor subtypes within the body, the compounds in accordance with the present invention may also be of benefit in enhancing cognitive function, and in treating and/or preventing cognitive disorders including presenile and senile dementia (also known as Alzheimer's disease and senile dementia of the Alzheimer type respectively).

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature (London)*, 1991, 350, 610) and $D_5$ (Sunahara et al., *Nature (London)*, 1991, 350, 614) receptor subtypes have been described.

The compounds in accordance with the present invention, being ligands for dopamine receptor subtypes within the body, in particular the $D_4$ receptor subtype, are accordingly of use in the treatment and/or prevention of disorders of the dopamine system, including schizophrenia.

The present invention provides a compound of formula I, or a salt or prodrug thereof:

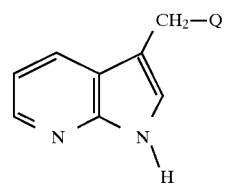

wherein Q represents a moiety of formula Qa or Qb:

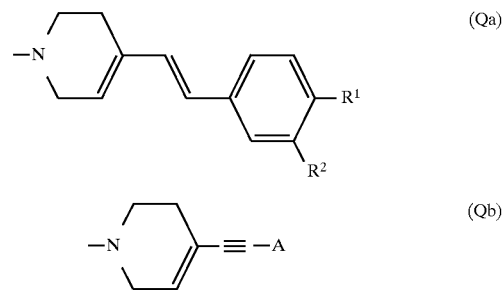

wherein
$R^1$ represents hydrogen, fluoro, cyano, trifluoromethyl, $C_{1-6}$ alkyl, $C_{1-6}$ alkoxy or di($C_{1-6}$)alkylamino; and
$R^2$ represents hydrogen, halogen, cyano, trifluoromethyl, $C_{1-6}$ alkyl or di($C_{1-6}$)alkylamino; or
$R^1$ and $R^2$ together represent methylenedioxy; provided that $R^1$ and $R^2$ are not both simultaneously hydrogen; and
A represents a group of formula (i), (ii) or (iii):

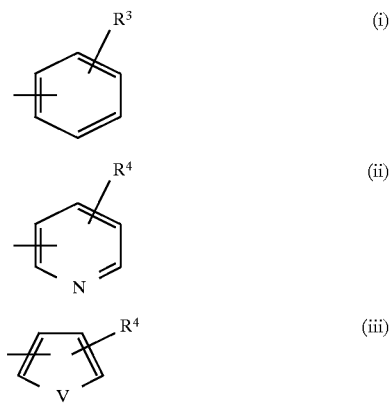

in which
V represents oxygen, sulphur or N—$R^5$;
$R^3$ represents halogen, cyano, trifluoromethyl, $C_{1-6}$ alkyl or $C_{1-6}$ alkoxy;
$R^4$ represents hydrogen, halogen, cyano, trifluoromethyl, $C_{1-6}$ alkyl or $C_{1-6}$ alkoxy; and
$R^5$ represents hydrogen or $C_{1-6}$ alkyl.

The compounds in accordance with the present invention are encompassed within the generic scope of co-pending International Patent Application No. PCT/GB94/00384 (published on 15 Sep. 1994 as WO 94/20459). There is, however, no specific disclosure therein of compounds corresponding to those of formula I above wherein Q is as defined above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

As used herein, the expression "$C_{1-6}$ alkyl" relates to methyl and ethyl groups, and straight-chained or branched propyl, butyl, pentyl and hexyl groups. Particular alkyl groups include methyl, ethyl, n-propyl, isopropyl and t-butyl. Derived expressions such as "$C_{1-6}$ alkoxy" and "di($C_{1-6}$)alkylamino" are to be construed accordingly.

The term "halogen" as used herein includes fluorine, chlorine, bromine and iodine, especially fluorine and chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. It is to be understood that all such isomers and mixtures thereof in any proportion are encompassed within the scope of the present invention.

Where the compounds of formula I above contain a moiety of formula Qa, the group $R^1$ suitably represents fluoro, cyano, trifluoromethyl, methyl, methoxy or dimethylamino. Particular values of $R^1$ include fluoro, cyano, trifluoromethyl, methyl and methoxy.

Suitably, $R^2$ represents fluoro, chloro, cyano, trifluoromethyl, methyl or dimethylamino, in particular fluoro or chloro, and especially chloro.

Moreover, one of $R^1$ and $R^2$ may represent hydrogen when the other of $R^1$ and $R^2$ is other than hydrogen. Preferably, one of $R^1$ and $R^2$ represents hydrogen and the other of $R^1$ and $R^2$ is other than hydrogen.

Where the compounds of formula I above contain a moiety of formula Qb, the integer V suitably represents sulphur.

Suitably, $R^3$ represents fluoro, chloro, cyano, trifluoromethyl, methyl or methoxy. Particular values of $R^3$ include fluoro, chloro, trifluoromethyl, methyl and methoxy.

Suitably, $R^4$ represents hydrogen, fluoro, chloro, cyano, trifluoromethyl, methyl or methoxy, especially hydrogen.

Suitably, $R^5$ represents hydrogen or methyl, especially methyl.

Particular values for the substituent A include fluorophenyl, chlorophenyl, cyanophenyl, trifluoromethylphenyl, methylphenyl, methoxyphenyl, pyridinyl and thienyl.

A particular sub-class of compounds according to the present invention is represented by the compounds of formula IIA, and salts and prodrugs thereof:

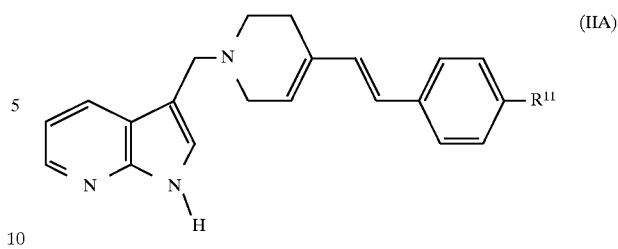

wherein $R^{11}$ represents fluoro, cyano, trifluoromethyl, $C_{1-6}$ alkyl, $C_{1-6}$ alkoxy or di($C_{1-6}$)alkylamino.

Suitably, $R^{11}$ represents fluoro, cyano, trifluoromethyl, methyl, methoxy or dimethylamino.

Particular values of $R^{11}$ include fluoro, cyano, trifluoromethyl, methyl and methoxy.

Another sub-class of compounds according to the present invention is represented by the compounds of formula IIB, and salts and prodrugs thereof:

(IIB)

wherein $R^{12}$ represents halogen, cyano, trifluoromethyl, $C_{1-6}$ alkyl or di($C_{1-6}$)alkylamino.

Suitably, $R^{12}$ represents fluoro, chloro, cyano, trifluoromethyl, methyl or dimethylamino.

Particular values of $R^{12}$ include fluoro and chloro, especially chloro.

A further sub-class of compounds according to the present invention is represented by the compounds of formula IIC, and salts and prodrugs thereof:

(IIC)

wherein $R^{11}$ is as defined with reference to formula IIA above; and $R^{22}$ represents fluoro, chloro, trifluoromethyl or $C_{1-6}$ alkyl.

Suitably, $R^{22}$ represents fluoro, chloro, trifluoromethyl or methyl.

Suitably, $R^{11}$ and $R^{22}$ both represent fluoro.

A still further sub-class of compounds according to the present invention is represented by the compounds of formula IID, and salts and prodrugs thereof:

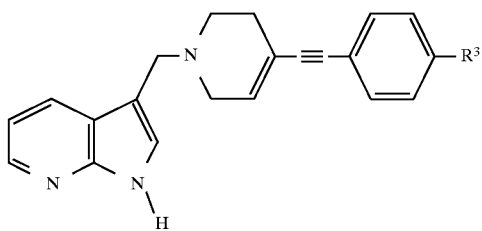

wherein R³ is as defined with reference to formula I above.

A yet further sub-class of compounds according to the present invention is represented by the compounds of formula I as defined above, and salts and prodrugs thereof, wherein Q represents a moiety of formula Qb in which A represents a pyridin-3-yl, thien-2-yl or thien-3-yl group.

Specific compounds within the scope of the present invention include:

3-[4-(4-trifluoromethylphenyl)ethynyl-1,2,3,6-tetrahydropyridin-1-yl]methyl-1H-pyrrolo[2,3-b]pyridine;
3-[4-(pyridin-3-yl)ethynyl-1,2,3,6-tetrahydropyridin-1-yl]methyl-1H-pyrrolo[2,3-b]pyridine;
3-[4-(4-methoxyphenyl)ethynyl-1,2,3,6-tetrahydropyridin-1-yl]methyl-1H-pyrrolo[2,3-b]pyridine;
3-[4-(4-methylphenyl)ethynyl-1,2,3,6-tetrahydropyridin-1-yl]methyl-1H-pyrrolo[2,3-b]pyridine;
3-[4-(4-fluorophenyl)ethynyl-1,2,3,6-tetrahydropyridin-1-yl]methyl-1H-pyrrolo[2,3-b]pyridine;
3-[4-(4-chlorophenyl)ethynyl-1,2,3,6-tetrahydropyridin-1-yl]methyl-1H-pyrrolo[2,3-b]pyridine;
3-[4-(thien-3-yl)ethynyl-1,2,3,6-tetrahydropyridin-1-yl]methyl-1H-pyrrolo[2,3-b]pyridine;
3-[4-(thien-2-yl)ethynyl-1,2,3,6-tetrahydropyridin-1-yl]methyl-1H-pyrrolo[2,3-b]pyridine;
(E)-3-[4-(2-(4-trifluoromethylphenyl)ethenyl)-1,2,3,6-tetrahydropyridin-1-yl]methyl-1H-pyrrolo[2,3-b]pyridine;
(E)-3-[4-(2-(4-methoxyphenyl)ethenyl)-1,2,3,6-tetrahydropyridin-1-yl]methyl-1H-pyrrolo[2,3-b]pyridine;
(E)-3-[4-(2-(4-methylphenyl)ethenyl)-1,2,3,6-tetrahydropyridin-1-yl]methyl-1H-pyrrolo[2,3-b]pyridine;
(E)-3-[4-(2-(4-cyanophenyl)ethenyl)-1,2,3,6-tetrahydropyridin-1-yl]methyl-1H-pyrrolo[2,3-b]pyridine;
(E)-3-[4-(2-(4-fluorophenyl)ethenyl)-1,2,3,6-tetrahydropyridin-1-yl]methyl-1H-pyrrolo[2,3-b]pyridine;
(E)-3-[4-(2-(3-chlorophenyl)ethenyl)-1,2,3,6-tetrahydropyridin-1-yl]methyl-1H-pyrrolo[2,3-b]pyridine;
and salts and prodrugs thereof.

Additional specific compounds within the scope of the present invention also include:
(E)-3-[4-(2-(3-fluorophenyl)ethenyl)-1,2,3,6-tetrahydropyridin-1-yl]methyl-1H-pyrrolo[2,3-b]pyridine;
(E)-3-[4-(2-(3,4-methylenedioxyphenyl)ethenyl)-1,2,3,6-tetrahydropyridin-1-yl]methyl-1H-pyrrolo[2,3-b]pyridine;
(E)-3-[4-(2-(3-methylphenyl)ethenyl)-1,2,3,6-tetrahydropyridin-1-yl]methyl-1H-pyrrolo[2,3-b]pyridine;
(E)-3-[4-(2-(3-cyanophenyl)ethenyl)-1,2,3,6-tetrahydropyridin-1-yl]methyl-1H-pyrrolo[2,3-b]pyridine;
(E)-3-[4-(2-(3,4-difluorophenyl)ethenyl)-1,2,3,6-tetrahydropyridin-1-yl]methyl-1H-pyrrolo[2,3-b]pyridine;
and salts and prodrugs thereof.

Further specific compounds within the scope of the present invention include:
(E)-3-[4-(2-(3-fluoro-4-methoxyphenyl)ethenyl)-1,2,3,6-tetrahydropyridin-1-yl]methyl-1H-pyrrolo[2,3-b]pyridine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

In order to alleviate the symptoms of schizophrenia without causing sedation or extrapyramidal side-effects, it is believed that the dosage level of the active ingredient should be selected such that the dose administered is effective in substantially completely blocking the dopamine $D_4$ receptor subtype in human brain whilst displaying no or negligible dopamine $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the compounds in accordance with this invention may be co-administered with another medicament, for example a known anti-schizophrenic agent which produces its effects via dopamine $D_2$ and/or $5-HT_2$ receptor blockade. Such co-administration may be desirable where a patient is already on an established treatment regime, for example one involving conventional anti-schizophrenic medicaments such as haloperidol or chlorpromazine.

The compounds in accordance with the present invention may be prepared by a process which comprises reacting a compound of formula III with a compound of formula IV:

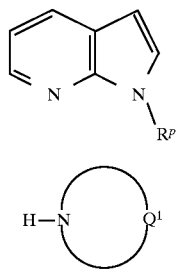

wherein $Q^1$ represents the residue of a moiety of formula Qa or Qb as defined above, and $R^P$ represents a hydrogen atom or a suitable protecting group; in the presence of a substantially equimolar amount of formaldehyde; followed, where required, by removal of the protecting group $R^P$.

The reaction is conveniently carried out by stirring the reactants in aqueous acetic acid, ideally in the presence of a buffer such as sodium acetate trihydrate, suitably at room temperature.

The formaldehyde may be utilised in the form of paraformaldehyde; or as a solution of formaldehyde in an inert solvent, e.g. 37% aqueous formaldehyde.

The protecting group $R^P$, when present, is suitably an acyl moiety such as acetyl, which can conveniently be removed as necessary by treatment under strongly basic conditions, e.g. sodium methoxide in methanol. Alternatively, the protecting group $R^P$ may be a carbamoyl moiety such as t-butoxycarbonyl (BOC), which can conveniently be removed as necessary by treatment under mildly acidic conditions.

In an alternative procedure, the compounds according to the present invention may be prepared by a process which comprises reacting a compound of formula IV as defined above with a compound of formula V:

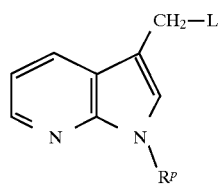

wherein $R^P$ is as defined above, and L represents a suitable leaving group; followed, where required, by removal of the protecting group $R^P$.

The leaving group L is suitably a halogen atom, e.g. chlorine or bromine; or a dialkylamino group, e.g. dimethylamino.

When L represents a halogen atom, the reaction between compounds IV and V is conveniently carried out by stirring the reactants under basic conditions in a suitable solvent, for example potassium carbonate in N,N-dimethylformamide, or triethylamine in tetrahydrofuran or acetonitrile. Where L represents a dialkylamino group, the reaction is conveniently effected by heating the reactants in an inert solvent such as toluene, typically at the reflux temperature of the solvent.

Where they are not commercially available, the starting materials of formula III, IV and V may be prepared by procedures analogous to those described in the accompanying Examples, or by standard methods well known from the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLE 1

3-[4-(4-Trifluoromethyl)phenylethynyl-1,2,3,6-tetrahydropyridin-1-yl]methyl-1H-[2,3-b]pyridine Step 1: 1-tert-Butoxycarbonyl-4-piperidone Triethylamine (92 ml, 0.66 mol) was added dropwise to a cold (0° C.) suspension of 4-piperidone monohydrate hydrochloride (100 g, 0.65 mol) and di-tert-butyl dicarbonate (142 g, 0,65 mol) in dichloromethane (400 ml) under a nitrogen atmosphere. The cooling bath was removed when about a quarter of the triethylamine had been added.

After 2 hours stirring at room temperature the vigorous bubbling had ceased, the mixture was diluted with water (500 ml), the phases were separated and the aqueous was extracted with dichloromethane (3×250 ml). The combined organics were washed with brine (250 ml), dried ($MgSO_4$) and evaporated in vacuo to give a light brown solid. The solid was dissolved in ethyl acetate (1 l) and treated with silica gel (150 g). Filtration and evaporation gave the title compound as a white waxy solid (111.7 g, 86%); $\delta_H$ ($CDCl_3$) 1.49 (9H, s, $OC(CH_3)_3$), 2.44 (4H, t, J 6.1 Hz, 2×piperidone $CH_2CO$) and 3.72 (4H, t, J 6.1 Hz, 2×piperidone $CH_2$—N).

Step 2: 1-tert-Butoxycarbonyl-4-trimethylsilylethynyl-1,2,3,6-tetrahydropyridine n-Butyl lithium (2.5M in hexanes, 110 ml, 276 mmol) was cannulated into a solution of trimethylsilylacetylene (40 ml, 276 mmol) in tetrahydrofuran (500 ml) at −70° C., under a nitrogen atmosphere, at such a rate that the temperature did not exceed −60° C. Once the addition was complete the solution was stirred at −70° C. for one hour. The cooling bath was removed and the solution was cannulated into a solution of 1-tert-butoxycarbonyl-4-piperidone in THF (500 ml) at −70° C. under a nitrogen atmosphere at such a rate that the temperature did not exceed −65°C. Once the addition was complete the mixture was stirred at −70° C. for 10 minutes before warming to room temperature. Following a one hour stir at room temperature the mixture was cooled to 0° C. and saturated ammonium chloride (500 ml) was added. The solvent was removed in vacuo and the residue extracted with dichloromethane (3×500 ml). The organics were dried ($MgSO_4$) and evaporated in vacuo to give an orange residue (89 g). The residue was dissolved in dichloromethane (1 l) under a nitrogen atmosphere, triethylamine (52.5 ml, 375 mmol) was added and the mixture was cooled to −10° C. Mesyl chloride was then added at such a rate that the temperature did not exceed 0° C. Once the addition was complete the mixture was stirred at 0° C. for 10 minutes, allowed to warm to room temperature and stirred for 20 hours.

The solution was treated with sodium bicarbonate (sat., 400 ml), the phases were separated and the aqueous extracted with dichloromethane (2×250 ml). The combined organics were washed with brine (250 ml), dried ($MgSO_4$) and evaporated in vacuo to give a pale oil which was purified by column chromatography on silica, eluting with ethyl acetate/petroleum ether 60/80 (1:1), to give the title compound (51 g, 72%) as a pale straw coloured oil; $\delta_H$ ($CDCl_3$) 1.46 (9H, s, $OC(CH_3)_3$), 2.24 (2H, br s, tetrahydropyridinyl $CH_2$), 3.47 (2H, t, J 5.6 Hz, tetrahydropyridinyl $CH_2$), 4.12 (2H, d, J 7.1 Hz, tetrahydropyridinyl $CH_2$) and 6.06 (1H, br s, tetrahydropyridinyl CH).

Step 3: 1-tert-Butoxycarbonyl-4-ethynyl-1,2,3,6-tetrahydroypridine

Potassium carbonate (1.0 g, 7.2 mmol) was added to a solution of 1-tert-butoxycarbonyl-4-trimethylsilylethynyl-1,2,3,6-tetrahydropyridine (44.9 g, 161 mmol) in methanol (250 ml) under a nitrogen atmosphere and the mixture was stirred at room temperature for 3 hours. The solution was evaporated in vacuo without heating. The residue was dissolved in ether (250 ml), washed with sodium carbonate (sat., 100 ml), water (50 ml) and brine (50 ml) before drying ($MgSO_4$) and evaporation in vacuo to give the title compound as a white waxy solid (30.0 g, 90%); $\delta_H$ ($CDCl_3$) 1.46 (9H, s, $OC(CH_3)_3$), 2.24–2.26 (2H, m, tetrahydropyridinyl $CH_2$), 2.89 (1H, s, ethynyl CH), 3.49 (2H, t, J 5.7 Hz, tetrahydropyridinyl $CH_2$), 3.95–3.97 (2H, m, tetrahydropyridinyl $CH_2$) and 6.10 (1H, s, tetrahydropyridinyl CH).

Step 4: 1-tert-Butoxycarbonyl-4-[(4-trifluoromethyl)-phenylethynyl]-1,2,3,6-tetrahydropyridine Bis(triphenylphosphine)palladium(II) chloride (61 mg, 0.09 mmol) and copper(I) iodide (17 mg, 0.09 mmol) were added to a solution of 1-tert-butoxycarbonyl-4-ethynyl-1,2,3,6-tetrahydropyridine (2.0 g, 9.6 mmol) and 4-iodobenzotrifluoride (3.15 g, 11.6 mmol) in diethylamine under a nitrogen atmosphere. The mixture was stirred at room temperature for 18 hours before evaporation in vacuo. The residue was diluted with dichloromethane (50 ml) and washed with water (50 ml). The aqueous was extracted with dichloromethane (2×50 ml) and the combined organics were washed with brine (50 ml), dried ($MgSO_4$) and evaporated in vacuo to give a red brown oil which solidified on standing. Purification by column chromatography on silica eluting with ethyl acetate/petrol (60°–80°) (1:9) gave the title compound as a beige solid (2.58 g, 76%); $\delta_H$ ($CDCl_3$) 2.24–2.30 (2H, m, tetrahydropyridinyl $CH_2$), 3.01 (2H, t, J 5.7 Hz, tetrahydropyridinyl $CH_2$), 6.23–6.26 (1H, m, tetrahydropyridinyl CH) and 7.49–7.58 (4H, m, ArH).

Step 5: 4-(4-Trifluoromethyl)phenylethynyl-1,2,3,6-tetrahydropyridine

Trifluoroacetic acid (10 ml) was added to a solution of 1-tert-butoxycarbonyl-4-[(4-trifluoromethyl)phenylethynyl]-1,2,3,6-tetrahydropyridine (2.40 g, 6.83 mmol) in dichloromethane (15 ml) under a nitrogen atmosphere and the solution was stirred at room temperature for 30 minutes. The mixture was evaporated in vacuo and the residue diluted with dichloromethane (40 ml) and washed with sodium hydroxide solution (1N, 40 ml). The aqueous was extracted with dichloromethane (2×40 ml) and the combined organics were washed with brine (40 ml), dried ($K_2CO_3$) and evaporated in vacuo to give the title compound as a yellow brown solid (1.69 g, 99%); $\delta_H$ ($CDCl_3$) 2.24–2.30 (2H, m, tetrahydropyridinyl $CH_2$), 3.01 (2H, t, J 5.7 Hz, tetrahydropyridinyl $CH_2$), 3.46–3.50 (2H, m, tetrahydropyridinyl $CH_2$), 6.24–6.26 (1H, m, tetrahydropyridinyl CH) and 7.49–7.58 (4H, m, ArH).

Step 6: 3-[(4-Trifluoromethyl)phenylethynyl-1,2,3,6-tetrahydropyridin-1-yl]methyl-1H-pyrrolo[2,3-b]pyridine A mixture of 4-(4-trifluoromethyl)phenylethynyl-1,2,3,6-tetrahydropyridine (800 mg, 3.2 mmol) and 3-dimethylaminomethyl-1H-pyrrolo[2,3-b]pyridine (613 mg, 3.5 mmol) in dry toluene (30 ml) under a nitrogen atmosphere was heated at reflux for 20 hours. The mixture was cooled to room temperature and the solid precipitate collected by filtration washed with toluene and dried in vacuo. The solid was recrystallised from toluene to give the title compound as a white solid (615 mg, 51%), m.p. 191°–193° C. (toluene); (found: C, 69.54; H, 4.65; N, 10.98. $C_{22}H_{18}F_3N_3$ requires C, 69.28; H, 4.76; N, 11.02%); $\delta_H$ (DMSO-$d_6$) 2.27–2.30 (2H, m, tetrahydropyridinyl $CH_2$), 2.58 (2H, t, J 5.6 Hz, tetrahydropyridinyl $CH_2$), 3.05 (2H, m, tetrahydropyridinyl $CH_2$), 3.73 (2H, s, $NCH_2Ar$), 6.24 (1H, m, tetrahydropyridinyl CH), 7.04 (1H, dd, J 7.8 & 4.6 Hz, 5-H), 7.38 (1H, d, J 2.3 Hz, 2-H), 7.62 (2H, d, J 8 Hz, ArH), 7.72 (2H, d, J 8 Hz, ArH), 8.02 (1H, dd, J 7.8 & 1.4 Hz, 4-H), 8.20 (1H, dd, J 4.6 & 1.5 Hz, 7-H) and 11.48 (1H, br s, NH); m/z ($ES^+$) 382 $(M+1)^+$.

EXAMPLE 2

3-[4-(4-Methoxy)phenylethynyl-1,2,3,6-tetrahydropyridin-1-yl]methyl-1H-pyrrol[2,3-b]pyridine M.p. 207°–209° C. (toluene); (found: C, 76.65; H, 6.08; N, 12.08. $C_{22}H_{21}N_3O$ requires C, 76.94; H, 6.16; N, 12.24%); $\delta_H$ (DMSO-$d_6$) 2.23 (2H, br s, tetrahydropyridinyl $CH_2$), 2.56 (2H, t, J 5.5 Hz, tetrahydropyridinyl $CH_2$), 3.02 (2H, d, J 2.9 Hz, tetrahydropyridinyl $CH_2$), 3.72 (2H, s, $NCH_2Ar$), 3.76 (3H, s, $OCH_3$), 6.08 (1H, m, tetrahydropyridinyl CH), 6.90–6.93 (2H, m, ArH), 7.03 (1H, dd, J 7.8 & 4.6 Hz, 5-H), 7.33–7.38 (3H, m, ArH), 8.02 (1H, dd, J 7.8 & 1.3 Hz, 4-H), 8.19 (1H, dd, J 4.6 & 1.5 Hz, 6-H) and 11.47 (1H, br s, NH); m/z (ES$^+$) 344 (M+1)$^+$.

EXAMPLE 3

3-[4-(3-Pyridinyl)ethynyl-1,2,3,6-tetrahydropyridin-1-yl]methyl-1H-pyrrolo[2,3-b]pyridine The title compound was synthesised from 3-iodopyridine prepared using the procedure of L. O. Shnaidmann et al., *Tr. Inst. Eksperim. Klinisch. Med. Akad. Nauk Latv. SSR,* 1962, 27, 1–14) using chemistry analogous to Example 1.

M.p. 170°–172° C. (toluene); (found: C, 76.28; H, 5.69; N, 17.34. $C_{20}H_{18}N_4 \cdot 0.025$ ($C_7H_8$) requires C, 76.52; H, 5.79; N, 17.69%); $\delta_H$ (DMSO-$d_6$) 2.26–2.29 (2H, m, tetrahydropyridinyl $CH_2$), 2.58 (2H, t, J 5.6 Hz, tetrahydropyridinyl $CH_2$), 3.05 (2H, d, J 3.2 Hz, tetrahydropyridinyl $CH_2$), 3.73 (2H, s, $NCH_2Ar$), 6.21 (1H, br s, tetrahydropyridinyl CH), 7.04 (1H, dd, J 7.8 & 4.7 Hz, 5-H), 7.38–7.41 (2H, m, ArH), 7.81–7.84 (1H, m, ArH), 8.02 (1H, dd, J 7.8 & 1.3 Hz, 4-H), 8.19 (1H, dd, J 4.6 & 1.5 Hz, 6-H), 8.52 (1H, dd, J 4.8 & 1.6 Hz, ArH), 8.61 (1H, dd, J 2.1 & 0.6 Hz, ArH) and 11.48 (1H, br s, NH); m/z (ES$^+$) 315 (M+1)$^+$.

EXAMPLE 4

3-[4-(3-Thienyl)ethynyl-1,2,3,6-tetrahydropyridin-1-yl]methyl-1H-pyrrolo[2,3-b]pyridine M.p. 203°–205° C. (methanol); (found: C, 70.45; H, 5.23; N, 12.83. $C_{19}H_{17}N_3S \cdot 0.25$ ($H_2O$) requires C, 70.45; H, 5.45; N, 12.97%); $\delta_H$ (DMSO-$d_6$) 2.28 (2H, br s, tetrahydropyridinyl $CH_2$), 2.56 (2H, t, J 5.6 Hz, tetrahydropyridinyl $CH_2$), 3.02–3.03 (2H, m, tetrahydropyridinyl $CH_2$), 3.72 (2H, s, $NCH_2Ar$), 6.10 (1H, br s, tetrahydropyridinyl CH), 7.03 (1H, dd, J 7.8 & 4.6 Hz, 5-H), 7.12 (1H, dd, J 5.0 & 1.1 Hz, ArH), 7.37 (1H, s, 2-H), 7.58 (1H, dd, J 5.0 & 2.9 Hz, ArH), 7.72 (1H, dd, J 2.9 & 1.0 Hz, ArH), 8.02 (1H, dd, J 7.8 & 1.4 Hz, 4-H), 8.19 (1H, dd, J 4.6 & 1.5 Hz, 6-H) and 11.47 (1H, br s, NH); m/z (ES$^+$) 320 (M+1)$^+$.

EXAMPLE 5

3-[4-(4-Chloro)phenylethynyl-1,2,3,6-tetrahydropyridin-1-yl]methyl-1H-pyrrolo[2,3-b]pyridine M.p. 114°–116° C. (methanol); (found: C, 72.19; H, 5.29; N, 11.85. $C_{21}H_{18}N_3Cl$ requires C, 72.51; H, 5.22; N, 12.08%); $\delta_H$ (DMSO-$d_6$) 2.24 (2H, br s, tetrahydropyridinyl $CH_2$), 2.57 (2H, t, J 5.5 Hz, tetrahydropyridinyl $CH_2$), 3.03 (2H, d, J 3.2 Hz, tetrahydropyridinyl $CH_2$), 3.72 (2H, s, $NCH_2Ar$), 6.16 (1H, m, tetrahydropyridinyl CH), 7.03 (1H, dd, J 7.8 & 4.6 Hz, 5-H), 7.37 (1H, d, J 2.3 Hz, 2-H), 7.42 (4H, s, ArH), 8.02 (1H, dd, J 7.9 & 1.4 Hz, 4-H), 8.19 (1H, dd, J 4.7 & 1.6 Hz, 6-H) and 11.47 (1H, br s, NH); m/z (ES$^+$) 348 (M+1)$^+$.

EXAMPLE 6

3-[4-(4-Methyl)phenylethynyl-1,2,3,6-tetrahydropyridin-1-yl]methyl-1H-pyrrolo[2,3-b]pyridine M.p. 219°–221° C. (methanol); (found: C, 79.80; H, 6.39; N, 12.64. $C_{22}H_{21}N_3 \cdot 0.2$ ($H_2O$) requires C, 79.82; H, 6.52; N, 12.69%); $\delta_H$ (DMSO-$d_6$) 2.23 (2H, br s, tetrahydropyridinyl $CH_2$), 2.30 (3H, s, $ArCH_3$), 2.56 (2H, t, J 5.6 Hz, tetrahydropyridinyl $CH_2$), 3.02 (2H, d, J 3.2 Hz, tetrahydropyridinyl $CH_2$), 3.72 (2H, s, $NCH_2Ar$), 6.10 (1H, m, tetrahydropyridinyl CH), 7.03 (1H, dd, J 7.8 & 4.7 Hz, 5-H), 7.17 (2H, m, ArH), 7.29 (2H, m, ArH), 7.37 (1H, d, J 2.3 Hz, 2-H), 8.02 (1H, dd, J 7.8 & 1.4 Hz, 4-H), 8.18 (1H, dd, J 4.7 & 1.5 Hz, 6-H) and 11.47 (1H, br s, NH); m/z (ES$^+$) 328 (M+1)$^+$.

EXAMPLE 7

3-[4-(4-Fluoro)phenylethynyl-1,2,3,6-tetrahydropyridin-1-yl]methyl-1H-pyrrolo[2,3-b]pyridine M.p. 191°–192° C. (methanol); (found: C, 75.98; H, 5.37; N, 12.54. $C_{21}H_{18}FN_3$ requires C, 76.11; H, 5.48; N, 12.68%); $\delta_H$ (DMSO-$d_6$) 2.24 (2H, m, tetrahydropyridinyl $CH_2$), 2.57 (2H, t, J 5.5 Hz, tetrahydropyridinyl $CH_2$), 3.03 (2H, d, J 3.0 Hz, tetrahydropyridinyl $CH_2$), 3.72 (2H, s, $NCH_2Ar$), 6.14 (1H, br s, tetrahydropyridinyl CH), 7.04 (1H, dd, J 7.8 & 4.6 Hz, 5-H), 7.18–7.23 (2H, m, ArH), 7.38 (1H, s, 2-H), 7.44–7.48 (2H, m, ArH), 8.02 (1H, dd, J 7.8 & 1.5 Hz, 4-H), 8.19 (1H, dd, J 4.7 & 1.5 Hz, 6-H) and 11.47 (1H, br s, NH); m/z (ES$^+$) 332 (M+1)$^+$.

EXAMPLE 8

3-[4-(2-Thienyl)ethynyl-1,2,3,6-tetrahydropyridin-1-yl]methyl-1H-pyrrolo[2,3-b]pyridine Step 1: 4-(2-Thienyl)ethynyl-1,2,3,6-tetrahydropyridine A solution of 1-tert-butoxycarbonyl-4-(2-thienyl)ethynyl-1,2,3,6-tetrahydropyridine (530 mg, 1.8 mmol) (prepared in a manner analogous to Example 1) in diethyl ether (10 ml) at room temperature under a nitrogen atmosphere was treated with excess ethereal hydrogen chloride. Following a 3 hour stir at room temperature the dark mixture was diluted with water and extracted with diethyl ether (2×30 ml). The aqueous phase was made basic with potassium carbonate solution (sat.) and extracted with diethyl ether (3×50 ml). The extracts were dried ($K_2CO_3$) and evaporated in vacuo to give the title compound as a brown oil (267 mg, 77%); $\delta_H$ ($CDCl_3$) 2.24–2.29 (2H, m, tetrahydropyridinyl $CH_2$), 3.00 (2H, J 5.7 Hz, tetrahydropyridinyl $CH_2$), 3.45–3.47 (2H, m, tetrahydropyridinyl $CH_2$), 6.17–6.19 (1H, m, tetrahydropyridinyl CH), 6.94–6.97 (1H, m, ArH), 7.16–7.17 (1H, m, ArH) and 7.22–7.26 (1H, m, ArH).

Step 2: 3-[4-(2-Thienyl)ethynyl-1,2,3,6-tetrahydropyridin-1-yl]methyl-1H-pyrrolo[2,3-b]pyridine The title compound was prepared from 4-(2-thienyl)ethynyl-1,2,3,6-tetrahydropyridine using chemistry analogous to Example 1.

M.p. 191°–193° C. (methanol); (found: C, 71.38; H, 5.24; N, 13.01. $C_{19}H_{17}N_3S$ requires C, 71.44; H, 5.36; N, 13.16%); $\delta_H$ (DMSO-$d_6$) 2.36 (2H, br s, tetrahydropyridinyl $CH_2$), 2.56 (2H, t, J 5.6 Hz, tetrahydropyridinyl $CH_2$), 3.03 (2H, d, J 3.1 Hz, tetrahydropyridinyl $CH_2$), 3.72 (2H, s, $NCH_2Ar$), 6.15 (1H, br s, tetrahydropyridinyl CH), 7.02–7.07 (2H, m, ArH), 7.26 (1H, dd, J 3.6 & 1.2 Hz, ArH), 7.37 (1H, d, J 2.3 Hz, 2-H), 7.58 (1H, dd, J 5.1 & 1.0 Hz, ArH), 8.02 (1H, dd, J 7.8 Hz, 4-H), 8.19 (1H, dd, J 4.6 & 1.5 Hz, 6-H) and 11.47 (1H, br s, NH); m/z (ES$^+$) 320 (M+1)$^+$.

EXAMPLE 9

(E)-3-[4-[2-(4-Fluorophenyl)ethenyl]-1,2,3,6-tetrahydropyridin-1-yl]methylpyrrolo[2,3-b]pyridine Step 1: (E)-4-[2-(4-Fluorophenyl)ethenyl]pyridine A mixture of 4-picoline (15.6 ml, 161 mmol) and 4-fluorobenzaldehyde (20 g, 161 mmol) in acetic anhydride (125 ml) was heated at reflux overnight. The reaction was cooled and the solvent evaporated. Water (100 ml) was added to the residue, and the mixture stirred at room temperature for 30 minutes. Saturated sodium carbonate solution (100 ml) and ethyl acetate (150 ml) were then added, and stirring continued for a further 30 minutes. The two phases were separated, and the aqueous phase extracted with ethyl acetate (3×200 ml). The combined organic phases were dried (MgSO$_4$) and evaporated. The residue was purified by flash chromatography, eluting with 50% ethyl acetate/petrol (60°–80°). The appropriate fractions were combined and concentrated to yield (E)-4-[2-(4-fluorophenyl)ethenyl]pyridine (19 g, 60%) as a beige solid. $\delta_H$ (CDCl$_3$) 6.93 (1H, d, J 16.3 Hz, ArCHCH), 7.05–7.13 (2H, m, ArH), 7.26 (1H, d, J 16.3 Hz, ArCHCH), 7.34–7.36 (2H, m, ArH), 7.48–7.54 (2H, m, ArH) and 8.56–8.60 (2H, m, ArH).

Step 2: (E)-1-Benzyl-4-[2-(4-fluorophenyl)ethenyl]-1,2,3,6-tetrahydropyridine

To a solution of (E)-4-[2-(4-fluorophenyl)ethenyl] pyridine (18.75 g, 94.2 mmol) in dimethylformamide (30 ml) at 90° C. was added benzyl bromide (11.9 ml, 100 mmol) and the reaction stirred at 90° C. for 1 hour. The reaction was cooled to room temperature, diluted with ethanol (400 ml) and sodium borohydride (4 g, 105 mmol) added in portions. The reaction was stirred at room temperature for 2 hours, after which time the solvent was evaporated to a slurry. Methanol was added, and the resultant solid filtered and dried to yield (E)-1-benzyl-4-[2-(4-fluorophenyl)ethenyl]-1,2,3,6-tetrahydropyridine (12 g, 44%) as a white solid. $\delta_H$ (CDCl$_3$) 2.41 (2H, br s, tetrahydropyridinyl CH$_2$), 2.68 (2H, t, J 5.8 Hz, tetrahydropyridinyl CH$_2$), 3.14 (2H, br s, tetrahydropyridinyl CH$_2$), 3.63 (2H, s, NCH$_2$Ar), 5.80 (1H, br s, tetrahydropyridinyl 5-CH), 6.40 (1H, d, J 16.2 Hz, ArCHCHC), 6.69 (2H, d, J 16.2 Hz, ArCHCHC), 6.96–7.02 (2H, m, ArH) and 7.25–7.39 (7H, m, ArH).

Step 3: (E)-4-[2-(4-Fluorophenyl)ethenyl]-1,2,3,6-tetrahydropyridine hydrochloride To a solution of (E)-1-benzyl-4-[2-(4-fluorophenyl) ethenyl]-1,2,3,6-tetrahydropyridine (11.6 g, 37.5 mmol) in dichloromethane (500 ml) at 0° C. was added 1-chloroethyl chloroformate (4.85 ml, 45 mmol). The reaction was stirred initially at 0° C., and allowing it to warm to room temperature over 2 hours. The solvent was evaporated and methanol (500 ml) added. The mixture was heated at reflux for 1 hour, cooled to room temperature, and the solvent evaporated to a slurry. Diethyl ether was added and the resultant precipitate filtered and dried to yield (E)-4-[2-(4-fluorophenyl)ethenyl] -1,2,3,6-tetrahydropyridine hydrochloride (6.2 g, 69%) as a white solid. $\delta_H$ (DMSO-d$_6$) 2.49–2.53 (2H, m, tetrahydropyridinyl CH$_2$), 3.23 (2H, t, J 6.1 Hz, tetrahydropyridinyl CH$_2$), 3.69 (2H, br s, tetrahydropyridinyl CH$_2$), 5.90 (1H, br s, tetrahydropyridinyl 5-CH), 6.61 (1H, d, J 16.3 Hz, ArCHCHC), 6.92 (1H, d, J 16.3 Hz, ArCHCHC), 7.15–7.20 (2H, m, ArH), 7.55–7.59 (7H, m, ArH) and 9.45 (1H, br s, NH).

Step 4: (E)-3-[4-[2-(4-Fluorophenyl)ethenyl]-1,2,3,6-tetrahydropyridin-1-yl]methylpyrrolo[2,3-b]pyridine A mixture of 3-dimethylaminomethyl- 1H-pyrrolo[2,3-b] pyridine (1.57 g, 9 mmol) and (E)-4-[2-(4-fluorophenyl) ethenyl]-1,2,3,6-tetrahydropyridine (2 g, 9 mmol) in toluene (50 ml) was refluxed overnight. The hot solution was filtered, and the product crystallised from toluene to give (E)-3-[4-[2-(4-fluorophenyl)ethenyl]-1,2,3,6-tetrahydropyridin-1-yl]methylpyrrolo[2,3-b]pyridine (1.2 g, 40%). M.p. 211°–213° C. (isopropanol). (Found: C, 75.05; H, 5.99; N,12.27; C$_{21}$H$_{20}$FN$_3$, 0.15H$_2$O requires C, 75.04; H, 6.09; N, 12.50%); $\delta_H$ (DMSO-d$_6$) 2.29 (2H, br s, tetrahydropyridinyl CH$_2$), 2.61 (2H, t, J 5.6 Hz tetrahydropyridinyl CH$_2$), 3.06 (2H, br s, tetrahydropyridinyl CH$_2$), 3.73 (2H, s, NCH$_2$Ar), 5.87 (1H, br s, tetrahydropyridinyl 5-CH), 6.45 (1H, d, J 16.3 Hz, ArCHCHC), 6.83 (1H, d, J 16.3 Hz, ArCHCHC), 7.01–7.04 (1H, m, ArH), 7.14 (2H, t, J 8.9 Hz, ArH), 7.38 (1H, s, ArH), 7.47–7.51 (2H, m, ArH), 8.02 (1H, d, J 7.9 Hz, ArH), 8.18–8.20 (1H, m, ArH) and 11.45 (1H, br s, NH); m/z (CI$^+$, NH$_3$), 334 (M+1)$^+$.

EXAMPLE 10

(E)-3-[4-[2-(3-Chlorophenyl)ethenyl]-1,2,3,6-tetrahydropyridin-1-yl]methylpyrrolo[2,3-b]pyridine M.p. 208°–210° C. (isopropanol). (Found: C, 71.86; H, 5.74; N, 11.66; C$_{21}$H$_{20}$ClN$_3$ requires C, 72.09; H, 5.76; N, 12.01%). $\delta_H$ (DMSO-d6) 2.28 (2H, br s, tetrahydropyridinyl CH$_2$), 2.61 (2H, t, J 5.5 Hz tetrahydropyridinyl CH$_2$), 3.07 (2H, br s, tetrahydropyridinyl CH$_2$), 3.73 (2H, s, NCH$_2$Ar), 5.93 (1H, br s, tetrahydropyridinyl 5-CH), 6.44 (1H, d, J 16.3 Hz, ArCHCHC), 6.95–7.05 (2H, m, ArCHCHC, ArH), 7.24 (1H, d, J 8.1 Hz, ArH), 7.30–7.43 (3H, m, ArH), 7.54 (1H, s, ArH), 8.02 (1H, d, J 7.8 Hz, ArH), 8.19 (1H, d, J 4.6 Hz, ArH) and 11.45 (1H, br s, NH); m/z (CI$^+$, NH$_3$) 350 (M+1)$^+$.

EXAMPLE 11

(E)-3-[4-[2-(4-Cyanophenyl)ethenyl]-1,2,3,6-tetrahydropyridin-1-yl]methylpyrrolo[2,3-b]pyridine M.p. 213°–215° C. (toluene). (Found: C, 76.62; H, 5.76; N, 16.05; C$_{22}$H$_{20}$N$_4$, 0.25H$_2$O requires C, 76.61; H, 5.99; N, 16.24%). $\delta_H$ (DMSO-d$_6$) 2.31 (2H, br s, tetrahydropyridinyl CH$_2$), 2.62 (2H, t, J 5.6 Hz, tetrahydropryridinyl CH$_2$), 3.09 (2H, br s, tetrahydropyridinyl CH$_2$), 3.74 (2H, s, NCH$_2$Ar), 6.01 (1H, br s, tetrahydropyridinyl 5-CH), 6.52 (1H, d, J 16.2 Hz, ArCHCHC), 7.01–7.06 (2H, m, ArCHCHC, ArH), 7.38 (1H, d, J 2.3 Hz, ArH), 7.64 (2H, d, J 8.4 Hz, ArH), 7.75 (2H, d, J 8.4 Hz, ArH), 8.03 (1H, d, J 7.8 Hz, ArH), 8.18–8.20 (1H, m, ArH) and 11.46 (1H, br s, NH); m/z (CI$^+$, NH$_3$) 341 (M+1)$^+$.

EXAMPLE 12

(E)-3-[4-[2-(4-Methylphenyl)ethenyl]-1,2,3,6-tetrahydropyridin-1-yl]methylpyrrolo[2,3-b]pyridine M.p. 209°–212° C. (xylene). (Found: C, 80.18; H, 7.13; N, 12.57; C$_{23}$H$_{23}$N$_3$ requires C, 80.21; H, 7.04; N, 12.76%). $\delta_H$ (DMSO-d$_6$) 2.27–2.29 (5H, m, tetrahydropyridinyl CH$_2$, ArCH$_3$), 2.61 (2H, t, J 5.7 Hz, tetrahydropyridinyl CH$_2$), 3.06 (2H, br s, tetrahydropyridinyl CH$_2$), 3.73 (2H, s, NCH$_2$Ar), 5.84 (1H, br s, tetrahydropyridinyl 5-CH), 6.41 (1H, d, J 16.3 Hz, ArCHCHC), 6.82 (1H, d, J 16.2 Hz, ArCHCHC), 7.01–7.04 (1H, m, ArH), 7.12 (2H, d, J 8.0 Hz, ArH), 7.32–7.38 (3H, m, ArH), 8.03 (1H, d, J 8.0 Hz, ArH), 8.18–8.20 (1H, m, ArH) and 11.46 (1H, br s, NH); m/z (CI$^+$, NH$_3$) 330 (M+1)$^+$.

EXAMPLE 13

(E)-3-[4-[2-(4-Methoxyphenyl)ethenyl]-1,2,3,6-tetrahydropyridin-1-yl]methylpyrrolo[2,3-b]pyridine M.p. 201°–204° C. (xylene). (Found: C, 76.20; H, 6.62; N, 12.12; C$_{22}$H$_{23}$N$_3$O requires C, 76.49; H, 6.71; N, 12.16%). $\delta_H$ (DMSO-d$_6$) 2.25 (2H, br s, tetrahydropyridinyl CH$_2$), 2.60 (2H, t, J 5.7 Hz, tetrahydropyridinyl CH$_2$), 3.05 (2H, br s, tetrahydropyridinyl CH$_2$), 3.72 (2H, s, NCH$_2$Ar), 3.74 (3H, s, OCH$_3$), 5.81 (1h, br s, tetrahydropyridinyl 5-CH), 6.40 (1H, d, J 16.3 Hz, ArCHCHC), 6.73 (1H, d, J 16.3 Hz, ArCHCHC), 6.88 (2H, d, J 8.8 Hz, ArH), 7.01–7.05 (1H, m, ArH), 7.37 (1H, s, ArH), 7.38 (2H, d, J 8.8 Hz, ArH), 8.02 (1H, dd, J 7.8, 1.4 Hz, ArH), 8.19 (1H, dd, J 4.6, 1.5 Hz, ArH) and 11.45 (1H, br s, NH); m/z (ES$^+$) 346 (M+1)$^+$.

EXAMPLE 14

(E)-3-[4-[2-(4-Trifluoromethylphenyl)ethenyl]-1,2,3,6-tetrahydropyridin-1-yl]methylpyrrolo[2,3-b]pyridine M.p. 203°–205° C. (xylene). (Found: C, 68.70; H, 5.28; N, 10.98; C$_{23}$H$_{20}$F$_3$N$_3$ requires C, 68.92; H, 5.25; N, 10.96%). $\delta_H$ (DMSO-$_6$) 2.32 (2H, br s, tetrahydropyridinyl CH$_2$), 2.62 (2H, t, J 7.9 Hz, tetrahydropyridinyl CH$_2$), 3.09 (2H, br s, tetrahydropyridinyl CH$_2$), 3.74 (2H, s, NCH$_2$Ar), 5.99 (1H, br s, tetrahydropyridinyl 5-CH), 6.54 (1H, d, J 16.2 Hz, ArCHCHC), 7.01–7.09 (2H, m, ArCHCHC, ArH), 7.39 (1H, d, J 3.4 Hz, ArH), 7.66 (4H, s, 2'-H, 3'-H, 5'-H, 6'-H), 8.03 (1H, dd, J 10.4, 2 Hz, ArH), 8.19 (1H, dd, J 6.7, 2.3 Hz, ArH) and 11.49 (1H, br s, NH); m/z (ES$^+$) 384 (M+1)$^+$.

EXAMPLE 15

(E)-3-[4-[2-(3-Fluorophenyl)ethenyl]-1,2,3,6-tetrahydropyridin-1-yl]methylpyrrolo[2,3-b]pyridine M.p. 199°–201° C. (propan-2-ol); (Found: C, 75.42; H, 5.95; N, 12.86. C$_{21}$H$_{20}$FN$_3$ requires C, 75.65; H, 6.05; N, 12.60%); $\delta_H$ (DMSO-d$_6$) 2.29 (2H, m, tetrahydropyridinyl CH$_2$), 2.61 (2H, t, J 5.5 Hz, tetrahydropyridinyl CH$_2$), 3.07 (2H, br s, tetrahydropyridinyl CH$_2$), 3.72 (2H, s, ArCH$_2$N), 5.93 (1H, br s, tetrahydropyridinyl 5-CH), 6.45 (1H, d, J 16.2 Hz, ArCHCHC), 6.93–7.05 (3H, m, ArCHCHC, ArH), 7.26–7.39 (4H, m, ArH), 8.02 (1H, d, J 7.8 Hz, ArH), 8.19 (1H, dd, J 4.6, 1.5 Hz, ArH) and 11.48 (1H, br s, NH); m/z (ES$^+$) 334 (M+1)$^+$.

EXAMPLE 16

(E)-3-[4-[2-(3,4-Methylenedioxyphenyl)ethenyl]-1,2,3,6-tetrahydropyridin-1-yl]methylpyrrolo[2,3-]pyridine M.p. 206°–208° C. (propan-2-ol); (Found: C, 72.39; H, 5.80; N, 11.22. C$_{22}$H$_{21}$N$_3$O$_2$ requires C, 72.61; H, 5.95; N, 11.54%); $\delta_H$ (DMSO-d$_6$) 2.65 (2H, br s, tetrahydropyridinyl CH$_2$), 2.60 (2H, t, J 5.7 Hz, tetrahydropyridinyl CH$_2$), 3.05 (2H, br s, tetrahydropyridinyl CH$_2$), 3.72 (2H, s, ArCH$_2$N), 5.81 (1H, br s, tetrahydropyridinyl 5-CH), 5.99 (2H, s, OCH$_2$O), 6.37 (1H, d, J 16.2 Hz, ArCHCHC), 6.74 (1H, d, J 16.2 Hz, ArCHCHC), 6.82–6.89 (2H, m, ArH), 7.01–7.04 (1H, m, ArH), 7.11 (1H, s, ArH), 7.37 (1H, s, ArH), 8.02 (1H, d, J 8.7 Hz, ArH), 8.19 (1H, d, J 4.7 Hz, ArH) and 11.45 (1H, br s, NH); m/z (ES$^+$) 360 (M+1)$^+$.

EXAMPLE 17

(E)-3-[4-[2-(3-Methylphenyl)ethenyl]-1,2,3,6-tetrahydropyridin-1-yl]methylpyrrolo[2,3-b]pyridine M.p. 210°–212° C. (propan-2-ol); (Found: C, 80.37; H, 6.89; N, 12.64. C$_{22}$H$_{23}$N$_3$ requires C, 80.21; H, 7.04; N, 12.76%); $\delta_H$ (DMSO-d$_6$) 2.28 (2H, br s, tetrahydropyridinyl CH$_2$), 2.61 (2H, t, J 5.6 Hz, tetrahydropyridinyl CH$_2$), 3.07 (2H, br s, tetrahydropyridinyl CH$_2$), 3.73 (2H, s, ArCH$_2$N), 5.87 (1H, br s, tetrahydropyridmyl 5-CH), 6.41 (1H, d, J 16.3 Hz, ArCHCHC), 6.86 (1H, d, J 16.4 Hz, ArCHCHC), 7.01–7.04 (2H, m, ArH), 7.16–7.27 (3H, m, ArH), 7.38 (1H, s, ArH), 8.03 (1H, d, J 7.7 Hz, ArH), 8.19 (1H, d, J 4.7 Hz, ArH) and 11.46 (1H, br s, NH); m/z (ES$^+$) 330 (M+1)$^+$.

EXAMPLE 18

(E)-3-[4-[2-(3-Cyanophenyl)ethenyl]-1,2,3,6-tetrahydropyridin-1-yl]methylpyrrolo[2,3-b]pyridine M.p. 213°–215° C. (propan-2-ol); (Found: C, 77.39; H, 5.77; N, 16.25. C$_{22}$H$_{20}$N$_4$ requires C, 77.62; H, 5.92; N, 16.46%); $\delta_H$ (DMSO-d$_6$) 2.29 (2H, br s, tetrahydropyridinyl CH$_2$), 2.62 (2H, t, J 5.7 Hz, tetrahydropyridinyl CH$_2$), 3.08 (2H, br s, tetrahydropyridinyl CH$_2$), 3.73 (2H, s, ArCH$_2$N), 5.96 (1H, br s, tetrahydropyridinyl 5-CH), 6.49 (1H, d, J 16.3 Hz, ArCHCHC), 7.02–7.08 (2H, m, ArCHCHC, ArH), 7.38 (1H, d, J 2.4 Hz, ArH), 7.51 (1H, t, J 7.8 Hz, ArH), 7.64 (1H, d, J 7.7 Hz, ArH), 7.79 (1H, d, J 8.0 Hz, ArH), 7.94 (1H, br s, ArH), 8.03 (1H, d, J 7.9 Hz, ArH), 8.19 (1H, d, J 4.6 Hz, ArH) and 11.46 (1H, br s, NH); m/z (ES$^+$) 341 (M+1)$^+$.

EXAMPLE 19

(E)-3-[4-[2-(3,4-Difluorophenyl)ethenyl]-1,2,3,6-tetrahydropyridin-1-yl]methylpyrrolo[2,3-b]pyridine M.p. 208°–210° C. (propan-2-ol); (Found: C, 71.60; H, 5.36; N, 12.17. C$_{21}$H$_{19}$F$_2$N$_3$ requires C, 71.78; H, 5.45; N, 11.96%); $\delta_H$ (DMSO-d$_6$) 2.28 (2H, br s, tetrahydropyridinyl CH$_2$), 2.61 (2H, t, J 5.7 Hz, tetrahydropyridinyl CH$_2$), 3.07 (2H, br s, tetrahydropyridinyl CH$_2$), 3.73 (2H, s, ArCH$_2$N), 5.91 (1H, br s, tetrahydropyridinyl 5-CH), 6.43 (1H, d, J 16.2 Hz, ArCHCHC), 6.90 (1H, d, J 16.2 Hz, ArCHCHC), 7.01–7.04 (1H, m, ArH), 7.28–7.39 (3H, m, ArH), 7.54–7.60 (1H, m, ArH), 8.02 (1H, d, J 8.2 Hz, ArH), 8.19 (1H, dd, J 4.3, 1.6 Hz, ArH) and 11.46 (1H, br s, NH); m/z (ES$^+$) 352 (M+1)$^+$.

EXAMPLE 20

(E)-3-[4-[2-(3-Fluoro-4-methoxyphenyl)ethenyl]-1,2,3,6-tetrahydyropyridin-1-yl]methylpyrrolo[2,3-b]pyridine M.p. 199.5–201.5° C. (MeOH); (found: C, 73.12; H, 6.03; N, 11.53. C$_{22}$H$_{22}$FN$_3$O requires C, 72.71; H, 6.10; N, 11.56%); $\delta_H$ (DMSO-d$_6$) 2.28 (2H, br s, tetrahydropyridinyl CH$_2$), 2.61 (2H, t, J 5.7 Hz, tetrahydropyridinyl CH$_2$), 3.07 (2H, br s, tetrahydropyridinyl CH$_2$), 3.73 (2H, s, NCH$_2$Ar), 3.83 (3H, s, ArOCH$_3$), 5.85 (1H, m, tetrahydropyridinyl 5-CH), 6.39 (1H, d, J 16.2 Hz, CH=CHAr), 6.80 (1H, d, J 16.2 Hz, CH=CHAr), 7.04 (1H, dd, J 7.8, 4.6 Hz, 5-H), 7.10 (1H, t, J 8.7 Hz, 5'-H), 7.21 (1H, m, 6'-H), 7.35–7.39 (2H, m, 2-H, 2'-H), 8.03 (1H, dd, J 7.8, 1.4 Hz, 4-H), 8.20 (1H, dd, J 4.6, 1.4 Hz, 6-H), and 11.46 (1H, br s, NH); m/z (ES$^+$) 364 (M+1)$^+$.

We claim:

1. A compound of formula I, or a pharmaceutically acceptable salt or prodrug thereof:

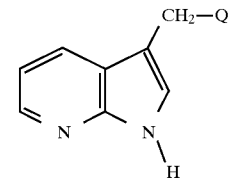

wherein Q represents a moiety of formula Qa or Qb:

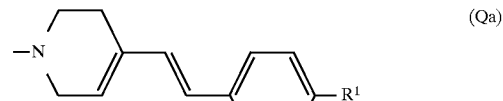

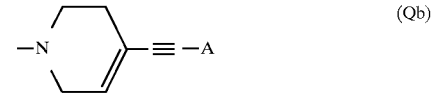

wherein $R^1$ represents hydrogen, fluoro, cyano, trifluoromethyl, $C_{1-6}$ alkyl, $C_{1-6}$ alkoxy or di($C_{1-6}$)alkylamino; and $R^2$ represents hydrogen, halogen, cyano, trifluoromethyl, $C_{1-6}$ alkyl or di($C_{1-6}$)alkylamino; or $R^1$ and $R^2$ together represent methylenedioxy; provided that $R^1$ and $R^2$ are not both simultaneously hydrogen; and A represents a group of formula (i), (ii) or (iii):

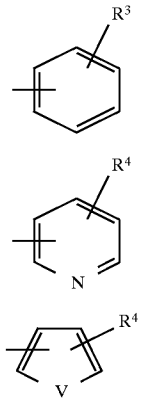

in which

V represents oxygen, sulphur or N—$R^5$;

$R^3$ represents halogen, cyano, trifluoromethyl, $C_{1-6}$ alkyl or $C_{1-6}$ alkoxy;

$R^4$ represents hydrogen, halogen, cyano, trifluoromethyl, $C_{1-6}$ alkyl or $C_{1-6}$ alkoxy; and $R^5$ represents hydrogen or $C_{1-6}$ alkyl.

2. A compound as claimed in claim 1 represented by formula IIA, and pharmaceutically acceptable salts or prodrugs thereof:

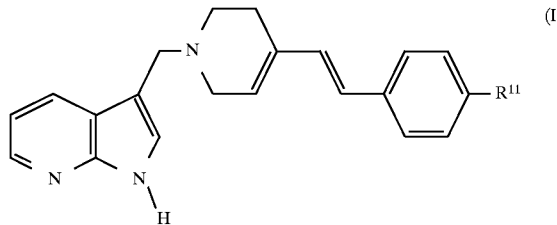

wherein $R^{11}$ represents fluoro, cyano, trifluoromethyl, $C_{1-6}$ alkyl, $C_{1-6}$ alkoxy or di($C_{1-6}$)alkylamino.

3. A compound as claimed in claim 1 represented by formula IIB, and pharmaceutically acceptable salts or prodrugs thereof:

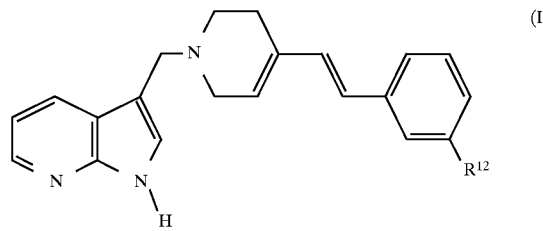

wherein $R^{12}$ represents halogen, cyano, trifluoromethyl, $C_{1-6}$ alkyl or di($C_{1-6}$)alkylamino.

4. A compound as claimed in claim 1 represented formula by Formula IIC, and pharmaceutically acceptable salts or prodrugs thereof:

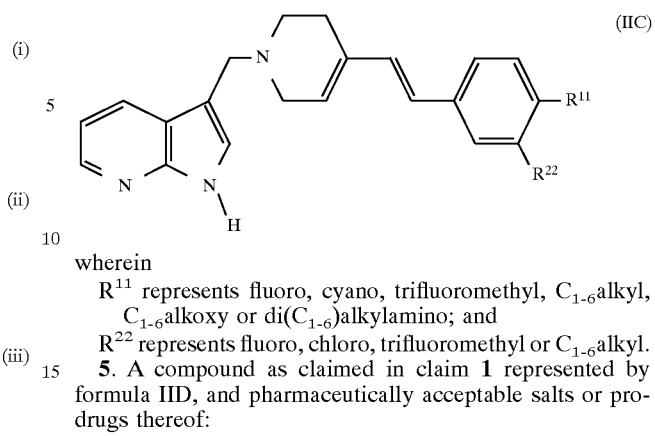

wherein $R^{11}$ represents fluoro, cyano, trifluoromethyl, $C_{1-6}$alkyl, $C_{1-6}$alkoxy or di($C_{1-6}$)alkylamino; and $R^{22}$ represents fluoro, chloro, trifluoromethyl or $C_{1-6}$alkyl.

5. A compound as claimed in claim 1 represented by formula IID, and pharmaceutically acceptable salts or prodrugs thereof:

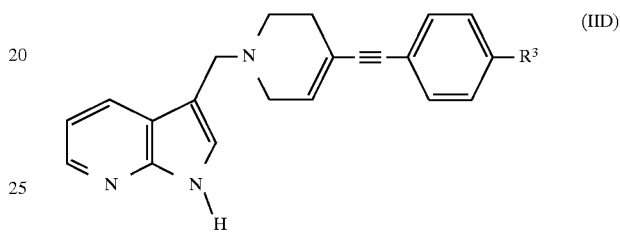

wherein $R^3$ is as defined in claim 1.

6. A compound as claimed in claim 1 wherein Q represents a moiety of formula Qb in which A represents a pyridin-3-yl, thien-2-yl or thien-3-yl group.

7. A compound selected from:
3-[4-(4-trifluoromethylphenyl)ethynyl-1,2,3,6-tetrahydropyridin-1-yl]methyl-1H-pyrrolo[2,3-b]pyridine;
3-[4-(pyridin-3-yl)ethynyl-1,2,3,6-tetrahydropyridin-1-yl]methyl-1H-pyrrolo[2,3-b]pyridine;
3-[4-(4-methoxyphenyl)ethynyl-1,2,3,6-tetrahydropyridin-1-yl]methyl-1H-pyrrolo[2,3-b]pyridine;
3-[4-(4-methylphenyl)ethynyl-1,2,3,6-tetrahydropyridin-1-yl]methyl-1H-pyrrolo[2,3-b]pyridine;
3-[4-(4-fluorophenyl)ethynyl-1,2,3,6-tetrahydropyridin-1-yl]methyl-1H-pyrrolo[2,3-b]pyridine;
3-[4-(4-chlorophenyl)ethynyl-1,2,3,6-tetrahydropyridin-1-yl]methyl-1H-pyrrolo[2,3-b]pyridine;
3-[4-(thien-3-yl)ethynyl-1,2,3,6-tetrahydropyridin-1-yl]methyl-1H-pyrrolo[2,3-b]pyridine;
3-[4-(thien-2-yl)ethynyl-1,2,3,6-tetrahydropyridin-1-yl]methyl-1H-pyrrolo[2,3-b]pyridine;
(E)-3-[4-(2-(4-trifluoromethylphenyl)ethenyl)-1,2,3,6-tetrahydropyridin-1-yl]methyl-1H-pyrrolo[2,3-b]pyridine;
(E)-3-[4-(2-(4-methoxyphenyl)ethenyl)-1,2,3,6-tetrahydropyridin-1-yl]methyl-1H-pyrrolo[2,3-b]pyridine;
(E)-3-[4-(2-(4-methylphenyl)ethenyl)-1,2,3,6-tetrahydropyridin-1-yl]methyl-1H-pyrrolo[2,3-b]pyridine;
(E)-3-[4-(2-(4-cyanophenyl)ethenyl)-1,2,3,6-tetrahydropyridin-1-yl]methyl-1H-pyrrolo[2,3-b]pyridine;
(E)-3-[4-(2-(4-fluorophenyl)ethenyl)-1,2,3,6-tetrahydropyridin-1-yl]methyl-1H-pyrrolo[2,3-b]pyridine;
(E)-3-[4-(2-(3-chlorophenyl)ethenyl)-1,2,3,6-tetrahydropyridin-1-yl]methyl-1H-pyrrolo[2,3-b]pyridine;
and pharmaceutically acceptable salts or prodrugs thereof.

8. A compound selected from:
(E)-3-[4-(2-(3-fluorophenyl)ethenyl)-1,2,3,6-tetrahydropyridin-1-yl]methyl-1H-pyrrolo[2,3-b]pyridine;
(E)-3-[4-(2-(3,4-methylenedioxyphenyl)ethenyl)-1,2,3,6-tetrahydropyridin-1-yl]methyl-1H-pyrrolo[2,3-b]pyridine;
(E)-3-[4-(2-(3-methylphenyl)ethenyl)-1,2,3,6-tetrahydropyridin-1-yl]methyl-1H-pyrrolo[2,3-b]pyridine;

(E)-3-[4-(2-(3-cyanophenyl)ethenyl)-1,2,3,6-tetrahydropyridin-1-yl]methyl-1H-pyrrolo[2,3-b]pyridine;
(E)-3-[4-(2-(3,4-difluorophenyl)ethenyl)-1,2,3,6-tetrahydropyridin-1-yl]methyl-1H-pyrrolo[2,3-b]pyridine;
and pharmaceutically acceptable salts or prodrugs thereof.

9. A compound selected from:
(E)-3-[4-(2-(3-fluoro-4-methoxyphenyl)ethenyl)-1,2,3,6-tetrahydropyridin-1-yl]methyl-1H-pyrrolo[2,3-b]pyridine;
and pharmaceutically acceptable salts and prodrugs thereof.

10. A pharmaceutical composition comprising a compound as claimed in claim 1 in association with a pharmaceutically acceptable carrier.

11. A composition as claimed in claim 10 further comprising haloperidol or chlorpromazine.

12. A process for the preparation of a compound as claimed in claim 1 which comprises:

(A) reacting a compound of formula III with a compound of formula IV:

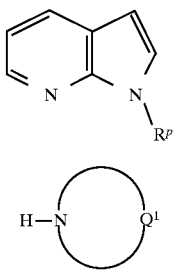

wherein $Q^1$ represents the residue of a moiety of formula Qa or Qb as defined in claim 1, and $R^P$ represents a hydrogen atom or a suitable protecting group; in the presence of a substantially equimolar amount of formaldehyde; followed, where required, by removal of the protecting group $R^P$; or (B) reacting a compound of formula IV as defined above with a compound of formula V:

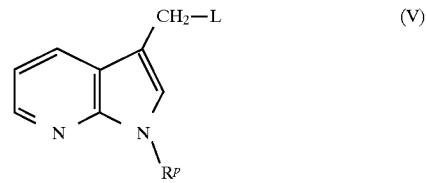

wherein $R^P$ is as defined above, and L represents a suitable leaving group; followed, where required, by removal of the protecting group $R^P$.

13. A method for the treatment and/or prevention of disorders of the dopamine system which comprises administering to a patient in need of such treatment an effective amount of a compound as claimed in claim 1.

* * * * *